US00PP10999P

United States Patent [19]

Evers

[11] Patent Number: Plant 10,999

[45] Date of Patent: Jul. 6, 1999

[54] HYBRID TEA ROSE PLANT NAMED 'TANALEDEV'

[75] Inventor: Hans Jürgen Evers, Uetersen, Germany

[73] Assignee: Bear Creek Gardens, Inc., Medford, Oreg.

[21] Appl. No.: 09/016,091

[22] Filed: Jan. 30, 1998

[51] Int. Cl.[6] ..... A01H 5/00

[52] U.S. Cl. ..... Plt./133

[58] Field of Search ..... Plt./133, 134, 144, Plt./145

*Primary Examiner*—Howard J. Locker

*Attorney, Agent, or Firm*—Klarquist Sparkman Campbell Leigh & Whinston, LLP

[57] ABSTRACT

Hybrid tea rose plant having an attractive ivory white flower color; large flowers on long stems; long vase life; and good cut flower production.

1 Drawing Sheet

The present invention relates to a new and distinct variety of rose plant of the hybrid tea class which was originated by me by crossing an unnamed white hybrid tea seedling (not patented), the parentage of which is not known, with TANweisa (not patented).

The primary objective of this breeding was to produce a new rose variety having novel ivory white flowers, long stems, good cut flower production, long vase life and large flower size. The objective was substantially achieved, along with other desirable improvements, as evidenced by the following unique combination of characteristics that are outstanding in the new variety and that distinguish it from its parents, as well as from all other varieties of which I am aware:

1. Ivory white flower color;
2. Long stems;
3. Large flower size;
4. Good cut flower production;
5. Exceptionally long vase life.

TANaledev produces 170–180 long stems/m$^2$, when grown in a greenhouse, bearing ivory white flowers.

Asexual reproduction of this new variety by budding, as performed at Wasco, Calif., and Uetersen, Germany, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—Unnamed white hybrid tea seedling (not patented), the parentage of which is not known.

*Pollen parent*.—TANweisa (not patented).

Classification:

*Botanical*.—Rosa hybrida.

*Commercial*.—Hybrid tea.

Flower

Observations made from specimens grown in greenhouse environments at Uetersen, Germany, and at Somis, Calif., from January 1997 to January 1998.

Blooming habit: Continuous.

Bud:

*Size*.—1¾" long when the petals start to unfurl.

*Form*.—Long, pointed ovoid.

*Color*.—When sepals first divide, bud color is Yellow White Group 158C. When half blown, the upper sides of the petals are Yellow White Group 158C, the lower sides of the petals are Yellow White Group 158C.

*Sepals*.—Color: Green Group 138B. Surface texture: Covered in fine hairs. There are three normally to heavily appendaged sepals. There are two unappendaged sepals with hairy edges.

*Receptacle*.—Color: Green Group 143C. Shape: Funnel. Size: Small (⅜"×¼"). Surface: Smooth.

*Peduncle*.—Length: Long (5½"). Surface: Slightly prickly. Color: Medium green. Strength: Stiff, erect.

Bloom:

*Size*.—Large. Average open size is 4 to 4½".

*Borne*.—Singly.

*Stems*.—Long (26–30"), strong.

*Form*.—When first open: High centered. Permanence: Retains its form to the end, outer petals curl back, quill fashion.

*Petalage*.—Number of petals under normal conditions: 30–35.

*Color*.—The upper sides of the petals are Yellow White Group 158C. The reverse sides of the petals are Yellow White Group 158C. The base of each petal has a small (3/16"×3/16") Yellow Green Group 149D half moon at the point of attachment. The major color on the upper sides is Yellow White Group 158C.

*Variegations*.—Occasional greenish streak on the guard petals.

*Discoloration*.—There is no change in color as the flower opens on the plant or in the vase until petal drops.

*Fragrance*.—Slight.

Petals:

*Texture*.—Thick.

*Shape*.—Rounded.

*Form*.—Tips slightly recurved, edges slightly quilled.

*Arrangement*.—Imbricated. Petaloids in the center: None.

*Persistence*.—Petals drop off cleanly before drying.

*Lastingness*.—On the plant: Very long (10–12 days). As a cut flower: Very long (16–18 days).

Reproductive parts:

*Anthers*.—Size: Medium. Quantity: Many. Color: Yellow. Arrangement: Regular around styles.

*Filaments*.—Color: White.

*Pollen*.—Color: Lemon yellow.

*Styles*.—Color: White.

*Stigmas*.—Color: Greenish white.

Plant:

*Form*.—Bush.

*Growth*.—Very vigorous; upright; branching. At maturity, height is six feet, width is four feet.

Foliage:

*Number of leaflets on normal mid-stem leaves*.—Five.

*Size*.—Large (6½"×4½").

*Quantity*.—Abundant.

*Color*.—New foliage: Upper and lower sides: Greyed Red Group 178C, very quickly turning the green color of the mature leaf. Old foliage: Upper side: Green Group 139A.

Leaflets: Lower side: Green Group 139C.

*Shape*.—Pointed oval.

*Texture*.—Upper side: Smooth.

*Edge*.—Serrated.

*Serration*.—Single, small.

*Petiole rachis*.—Color: Green.

*Petiole underside*.—Rough with prickles.

*Stipules*.—Long (⅝"), serrated, bearded.

*Disease resistance*.—Resistant to mildew under normal growing conditions at Somis, Calif. and Uetersen, Germany.

Wood:

*New wood*.—Color: Reddish. Bark: Smooth.

*Old wood*.—Color: Green. Bark: Smooth.

Prickles:

*Quantity*.—On main canes from base: Ordinary. On laterals from main canes: Ordinary.

*Form*.—Medium, hooked downward.

*Color when young*.—Red.

Small prickles:

*Quantity*.—On main stalks: None. On laterals: None.

I claim:

1. A new and distinct variety rose plant of the hybrid tea class, as herein shown and described, characterized particularly by the unique combination of its attractive ivory white flower color; large flowers on long stems; long vase life; and good cut flower production.

* * * * *

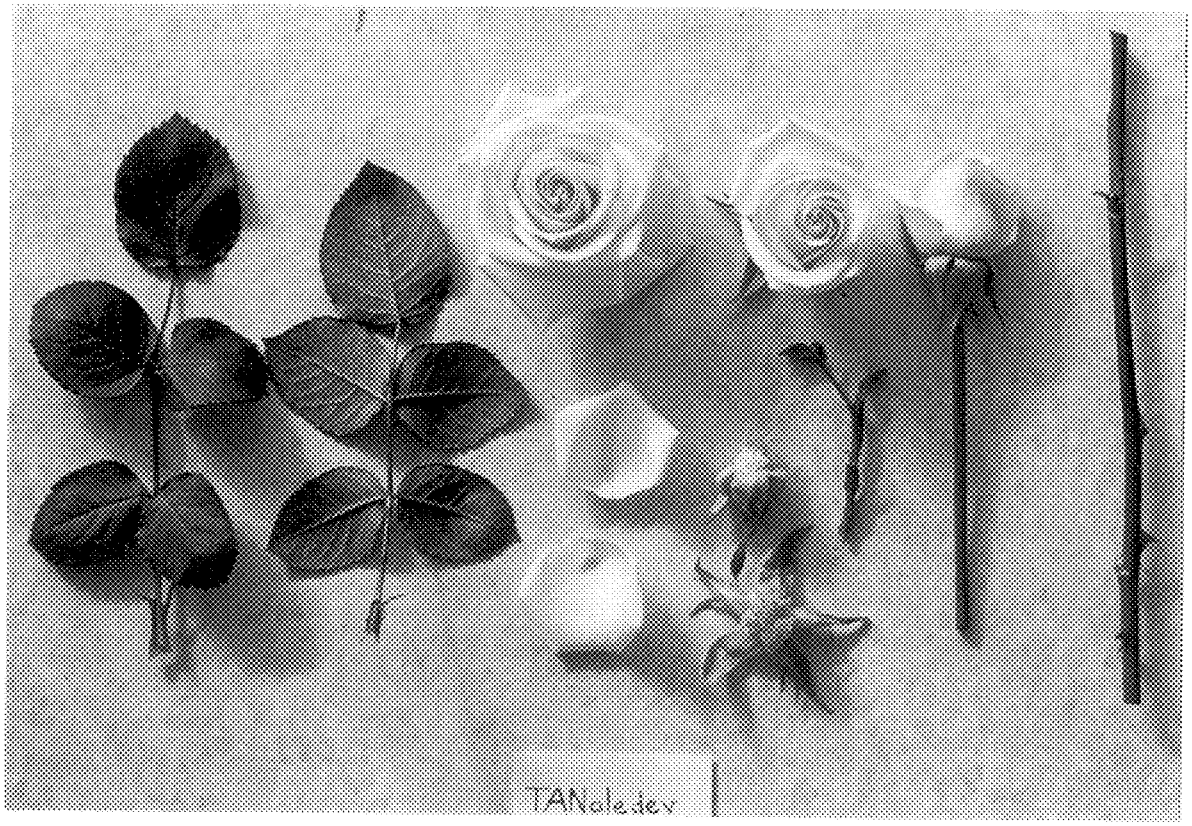
TANale.dev